US012770730B2

(12) United States Patent
Fuchigami et al.

(10) Patent No.: US 12,770,730 B2
(45) Date of Patent: Oct. 20, 2026

(54) INFORMATION PROCESSING APPARATUS, INFORMATION PROCESSING METHOD, INFORMATION PROCESSING PROGRAM, LEARNING DEVICE, LEARNING METHOD, LEARNING PROGRAM, AND DISCRIMINATIVE MODEL

(71) Applicant: FUJIFILM Corporation, Tokyo (JP)

(72) Inventors: Takuya Fuchigami, Tokyo (JP); Sadato Akahori, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 773 days.

(21) Appl. No.: 18/170,535

(22) Filed: Feb. 17, 2023

(65) Prior Publication Data

US 2023/0282336 A1 Sep. 7, 2023

(30) Foreign Application Priority Data

Mar. 7, 2022 (JP) ................................ 2022-034783

(51) Int. Cl.
*G16H 30/40* (2018.01)
*G06T 7/00* (2017.01)

(52) U.S. Cl.
CPC .......... *G16H 30/40* (2018.01); *G06T 7/0012* (2013.01); *G06T 2207/10081* (2013.01); *G06T 2207/30016* (2013.01)

(58) Field of Classification Search
CPC ...... G16H 30/40; G16H 50/20; G06T 7/0012; G06T 2207/10081; G06T 2207/30016; G06T 2207/20081; G06T 2207/20084
See application file for complete search history.

(56) References Cited

U.S. PATENT DOCUMENTS

| | | | | |
|---|---|---|---|---|
| 2010/0094133 | A1* | 4/2010 | Yoshiara | A61B 8/469 600/458 |
| 2019/0269359 | A1* | 9/2019 | Kim | G06T 7/0014 |
| 2020/0104995 | A1* | 4/2020 | Akahori | G06T 7/11 |
| 2020/0104996 | A1* | 4/2020 | Akahori | G16H 50/20 |
| 2022/0207720 | A1* | 6/2022 | Kim | G06T 7/0012 |
| 2024/0415472 | A1 | 12/2024 | Ishii et al. | |
| 2025/0131560 | A1* | 4/2025 | Lee | G16H 50/20 |

FOREIGN PATENT DOCUMENTS

| | | |
|---|---|---|
| JP | 2020054580 | 4/2020 |
| JP | 2021175454 | 11/2021 |
| WO | 2023171039 | 9/2023 |

OTHER PUBLICATIONS

"Notice of Reasons for Refusal of Japan Counterpart Application", issued on Sep. 30, 2025, with English translation thereof, pp. 1-5.

* cited by examiner

*Primary Examiner* — Iriana Cruz
(74) *Attorney, Agent, or Firm* — JCIPRNET

(57) ABSTRACT

A processor acquires a medical image and a first disease region in the medical image, derives a second disease region related to the first disease region in the medical image based on the medical image and the first disease region, updates the first disease region based on the medical image and the second disease region, updates the second disease region based on the medical image and the updated first disease region, and repeats update of the first disease region and update of the second disease region until a predetermined end condition is satisfied.

10 Claims, 13 Drawing Sheets

INFORMATION PROCESSING APPARATUS, INFORMATION PROCESSING METHOD, INFORMATION PROCESSING PROGRAM, LEARNING DEVICE, LEARNING METHOD, LEARNING PROGRAM, AND DISCRIMINATIVE MODEL

CROSS REFERENCE TO RELATED APPLICATIONS

The present application claims priority from Japanese Patent Application No. 2022-034783, filed on Mar. 7, 2022, the entire disclosure of which is incorporated herein by reference.

BACKGROUND

Technical Field

The present disclosure relates to an information processing apparatus, an information processing method, an information processing program, a learning device, a learning method, a learning program, and a discriminative model.

Related Art

In recent years, with the progress of medical devices, such as a computed tomography (CT) apparatus and a magnetic resonance imaging (MM) apparatus, an image diagnosis can be made by using a medical image having a higher quality and a higher resolution. In particular, in a case in which a target part is the brain, it is possible to specify a region in which a blood vessel disorder of the brain, such as a cerebral infarction or a cerebral hemorrhage, occurs by the image diagnosis using a CT image, an MRI image, or the like. Therefore, various methods for supporting the image diagnosis have been proposed.

By the way, the cerebral infarction is a disease in which a brain tissue is damaged by occlusion of a cerebral blood vessel, and is known to have a poor prognosis. In a case in which the cerebral infarction is developed, irreversible cell death progresses with the elapse of time. Therefore, how to shorten the time to the start of treatment has become an important issue. Here, in the application of thrombectomy treatment method, which is a typical treatment method for the cerebral infarction, two pieces of information, “degree of extent of infarction” and “presence or absence of large vessel occlusion (LVO)”, are required (see Appropriate Use Guidelines For Percutaneous Transluminal Cerebral Thrombectomy Devices, 4th edition, March 2020, p. 12-(1)).

On the other hand, in the diagnosis of a patient suspected of having a brain disease, the presence or absence of bleeding in the brain is often confirmed before confirming the cerebral infarction. Since bleeding in the brain can be clearly confirmed on a non-contrast CT image, a diagnosis using the non-contrast CT image is first made for the patient suspected of having the brain disease. However, in the non-contrast CT image, a difference in pixel value between a region of the cerebral infarction and the other region is not so large. Moreover, in the non-contrast CT image, a hyperdense artery sign (HAS) reflecting a thrombus that causes the large vessel occlusion can be visually recognized, but is not clear, so that it is difficult to specify a large vessel occlusion part. As described above, it is often difficult to specify an infarction region and the large vessel occlusion part by using the non-contrast CT image. Therefore, after the diagnosis using the non-contrast CT image, the MRI image or a contrast CT image is acquired to diagnose whether or not the cerebral infarction has developed, specify the large vessel occlusion part, and confirm the degree of extent of the infarction in a case in which the cerebral infarction has occurred.

However, in a case in which whether or not the cerebral infarction has developed is diagnosed by acquiring the MRI image and the contrast CT image after the diagnosis using the CT image, the elapsed time from the development of the infarction is long and the start of treatment is delayed, as a result, there is a high probability that the prognosis will be poor.

Therefore, a method for automatically extracting an infarction region and the large vessel occlusion part from the non-contrast CT image has been proposed. For example, JP2020-054580A proposes a method of specifying an infarction region and a thrombus region by using a discriminator that has been trained to extract the infarction region from a non-contrast CT image and a discriminator that has been trained to extract the thrombus region from the non-contrast CT image.

On the other hand, an appearance place of HAS representing the large vessel occlusion part is changed depending on which blood vessel is occluded, and an appearance varies depending on an angle of a tomographic plane with respect to the brain in the CT image, a property of a thrombus, a degree of occlusion, and the like. Moreover, it may be difficult to distinguish from similar structures in the vicinity, such as calcification. Moreover, the infarction region is generated in a blood vessel dominant region by the blood vessel in which the HAS is generated. Therefore, in a case in which the large vessel occlusion part can be specified, it is easy to specify the infarction region. Moreover, the occlusion of the blood vessel occurs in an organ other than the brain, such as the heart as well as the brain.

SUMMARY OF THE INVENTION

The present disclosure has been made in view of the circumstances described above, and is to enable accurately specifying a first disease region, such as an infarction region, included in a medical image and a second disease region, such as an occlusion part, related to the first disease region.

The present disclosure relates to an information processing apparatus comprising at least one processor, in which the processor acquires a medical image and a first disease region in the medical image, derives a second disease region related to the first disease region in the medical image based on the medical image and the first disease region, updates the first disease region based on the medical image and the second disease region, updates the second disease region based on the medical image and the updated first disease region, and repeats update of the first disease region and update of the second disease region until a predetermined end condition is satisfied.

It should be noted that a case in which the first disease region and the second disease region consist of only one pixel is regarded as a region in the present disclosure, as well as a case in which the first disease region and the second disease region consist of a plurality of pixels in the medical image, and thus it is assumed that there may be a case in which the first disease region and the second disease region consisting of only one pixel may be derived.

It should be noted that, in the information processing apparatus according to the present disclosure, the processor may perform update of the first disease region and derivation and update of the second disease region by using a first discriminative model that has been trained to output the second disease region in a case in which the medical image and the first disease region are input, and a second discriminative model that has been trained to output the first disease region in a case in which the medical image and the second disease region are input.

Moreover, in the information processing apparatus according to the present disclosure, the processor may perform update of the first disease region and derivation and update of the second disease region further based on at least one of information representing an anatomical region of an organ including the first and second disease regions or clinical information.

Moreover, in the information processing apparatus according to the present disclosure, the processor may acquire the first disease region by extracting the first disease region from the medical image.

Moreover, in the information processing apparatus according to the present disclosure, the processor may derive quantitative information for at least one of the first disease region or the second disease region, and may display the quantitative information.

Moreover, in the information processing apparatus according to the present disclosure, the medical image may be a non-contrast CT image of a brain of a patient, the first disease region may be any one of an infarction region or a large vessel occlusion part in the non-contrast CT image, and the second disease region may be the other of the infarction region or the large vessel occlusion part in the non-contrast CT image.

Moreover, in the information processing apparatus according to the present disclosure, the processor may perform derivation and update of the second disease region by further using first information of regions symmetrical with respect to a midline of the brain in at least the non-contrast CT image out of the non-contrast CT image and the first disease region, and may perform update of the first disease region by further using second information of regions symmetrical with respect to the midline of the brain in at least the non-contrast CT image out of the non-contrast CT image and the second disease region.

Moreover, in the information processing apparatus according to the present disclosure, the first information may be first reversal information obtained by reversing at least the non-contrast CT image out of the non-contrast CT image and the first disease region with respect to the midline of the brain, and the second information may be second reversal information obtained by reversing at least the non-contrast CT image out of the non-contrast CT image and the second disease region with respect to the midline of the brain.

The present disclosure relates to a learning device comprising at least one processor, in which the processor acquires training data including input data consisting of a medical image including a first disease region and the first disease region in the medical image, and correct answer data consisting of a second disease region related to the first disease region in the medical image, and constructs a discriminative model that outputs the second disease region in a case in which the medical image and the first disease region are input, by subjecting a neural network to machine learning using the training data.

The present disclosure relates to a discriminative model that outputs, in a case in which a medical image and a first disease region in the medical image are input, a second disease region related to the first disease region in the medical image.

The present disclosure relates to an information processing method comprising acquiring a medical image and a first disease region in the medical image, deriving a second disease region related to the first disease region in the medical image based on the medical image and the first disease region, updating the first disease region based on the medical image and the second disease region, updating the second disease region based on the medical image and the updated first disease region, and repeating update of the first disease region and update of the second disease region until a predetermined end condition is satisfied.

The present disclosure relates to a learning method comprising acquiring training data including input data consisting of a medical image including a first disease region and the first disease region in the medical image, and correct answer data consisting of a second disease region related to the first disease region in the medical image, and constructing a discriminative model that outputs the second disease region in a case in which the medical image and the first disease region are input, by subjecting a neural network to machine learning using the training data.

It should be noted that programs casing a computer to execute the information processing method and the learning method according to the present disclosure may be provided.

According to the present disclosure, the first disease region included in the medical image and the second disease region related to the first disease region can be accurately specified.

DETAILED DESCRIPTION

Figure 1:
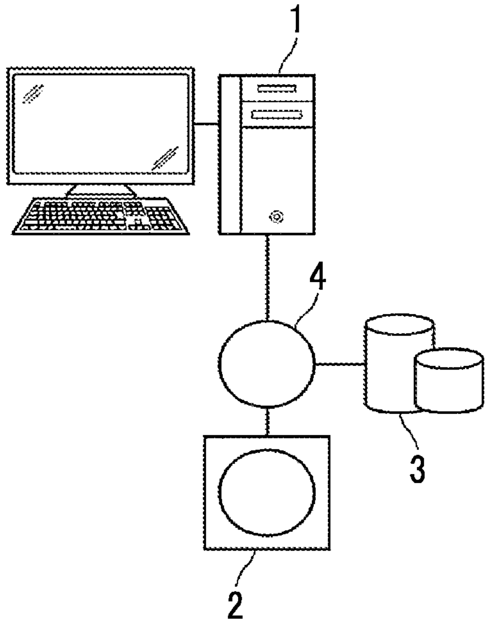
FIG. 1 is a diagram showing a schematic configuration of a medical information system to which an information processing apparatus and a learning device according to a first embodiment of the present disclosure are applied.

In the following, a first embodiment of the present disclosure will be described with reference to the drawings. FIG. 1 is a hardware configuration diagram showing an outline of a diagnosis support system to which an information processing apparatus and a learning device according to the first embodiment of the present disclosure are applied. As shown in FIG. 1, in the diagnosis support system, an information processing apparatus 1, a three-dimensional image capturing apparatus 2, and an image storage server 3 according to the first embodiment are connected to each other in a communicable state via a network 4. It should be noted that the information processing apparatus 1 includes the learning device according to the present embodiment.

The three-dimensional image capturing apparatus 2 is an apparatus that images a diagnosis target part of a subject to generate a three-dimensional image representing the part, and is, specifically, a CT apparatus, an Mill apparatus, a PET apparatus, and the like. A medical image generated by the three-dimensional image capturing apparatus 2 is transmitted to and stored in the image storage server 3. It should be noted that, in the present embodiment, the diagnosis target part of a patient who is the subject is the brain, the three-dimensional image capturing apparatus 2 is the CT apparatus, and a three-dimensional CT image G0 of the head of the patient who is the subject is generated in the CT apparatus. It should be noted that, in the present embodiment, the CT image G0 is a non-contrast CT image acquired by performing imaging without using a contrast agent.

The image storage server 3 is a computer that stores and manages various data, and comprises a large-capacity external storage device and software for database management. The image storage server 3 communicates with another device via the wired or wireless network 4 to transmit and receive image data and the like to and from the other device. Specifically, the image storage server 3 acquires various data including the image data of the CT image generated by the three-dimensional image capturing apparatus 2 via the network, and stores and manages the data in a recording medium, such as the large-capacity external storage device. Moreover, training data for constructing a discriminative model is also stored in the image storage server 3, as will be described below. It should be noted that a storage format of the image data and the communication between the devices via the network 4 are based on a protocol, such as digital imaging and communication in medicine (DICOM).

Figure 2:
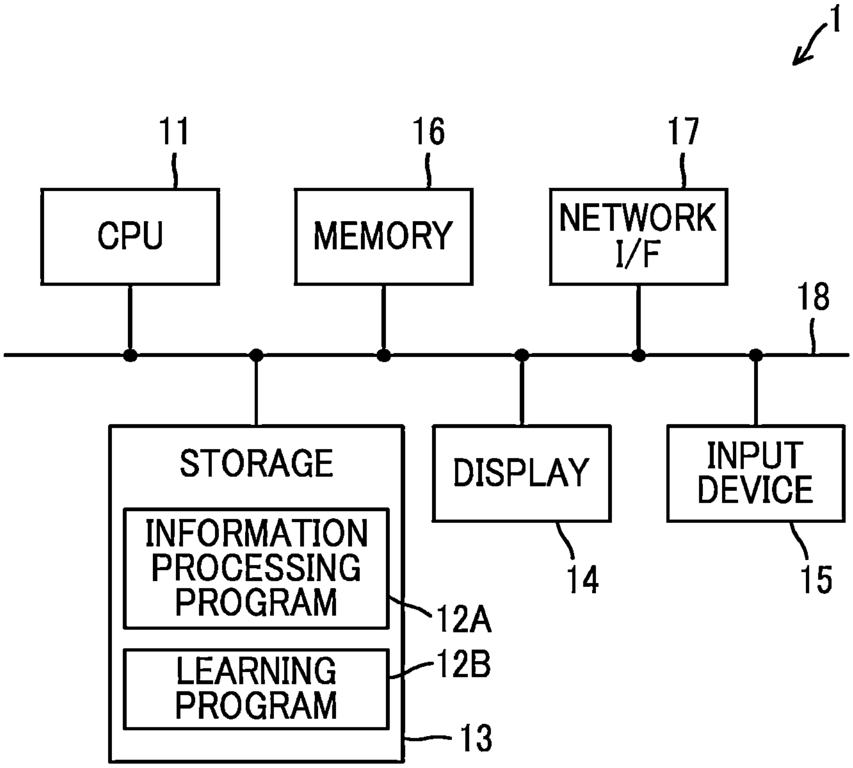
FIG. 2 is a diagram showing a schematic configuration of the information processing apparatus and the learning device according to the first embodiment.

Next, the information processing apparatus and the learning device according to the first embodiment of the present disclosure will be described. FIG. 2 shows a hardware configuration of the information processing apparatus and the learning device according to the first embodiment. As shown in FIG. 2, the information processing apparatus and the learning device (hereinafter, represented by the information processing apparatus) 1 includes a central processing unit (CPU) 11, a non-volatile storage 13, and a memory 16 as a transitory storage area. Moreover, the information processing apparatus 1 includes a display 14, such as a liquid crystal display, an input device 15, such as a keyboard and a mouse, and a network interface (I/F) 17 connected to the network 4. The CPU 11, the storage 13, the display 14, the input device 15, the memory 16, and the network I/F 17 are connected to a bus 18. It should be noted that the CPU 11 is an example of a processor according to the present disclosure.

The storage 13 is realized by a hard disk drive (HDD), a solid state drive (SSD), a flash memory, or the like. An information processing program 12A and a learning program 12B are stored in the storage 13 as a storage medium. The CPU 11 reads out the information processing program 12A and the learning program 12B from the storage 13, expands the information processing program 12A and the learning program 12B in the memory 16, and executes the expanded information processing program 12A and learning program 12B.

Figure 3:
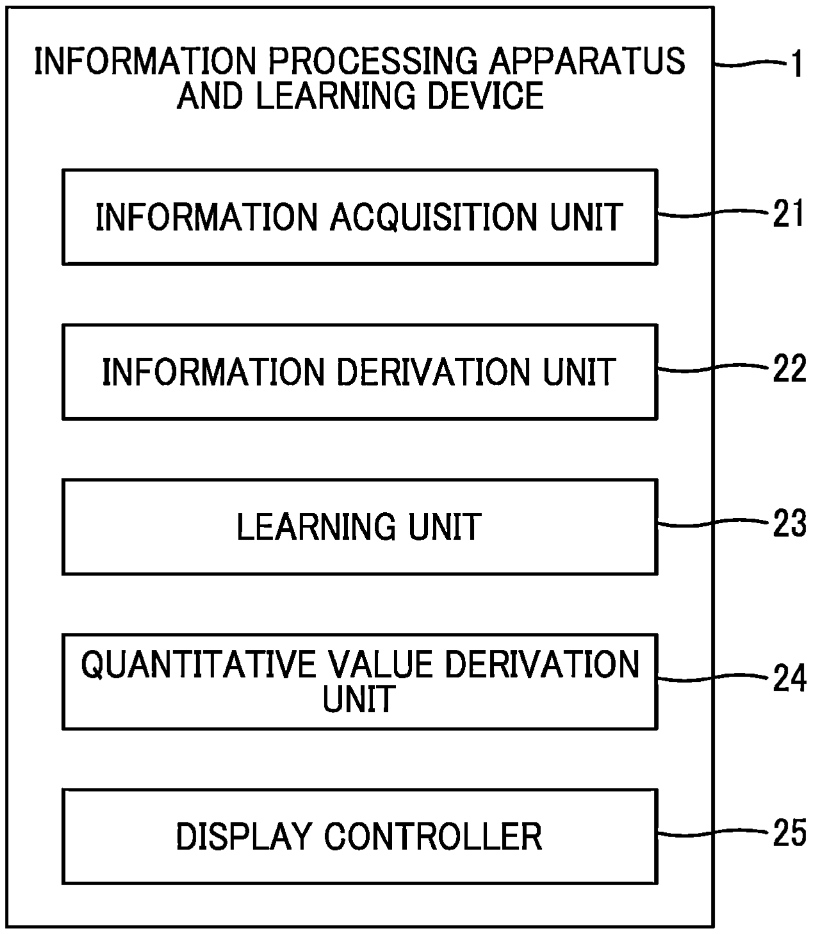
FIG. 3 is a functional configuration diagram of the information processing apparatus and the learning device according to the first embodiment.

Next, a functional configuration of the information processing apparatus according to the first embodiment will be described. FIG. 3 is a diagram showing the functional configuration of the information processing apparatus according to the first embodiment. As shown in FIG. 3, the information processing apparatus 1 comprises an information acquisition unit 21, an information derivation unit 22, a learning unit 23, a quantitative value derivation unit 24, and a display controller 25. Then, by executing the information processing program 12A, the CPU 11 functions as the information acquisition unit 21, the information derivation unit 22, the quantitative value derivation unit 24, and the display controller 25. Moreover, the CPU 11 functions as the learning unit 23 by executing the learning program 12B.

The information acquisition unit 21 acquires the non-contrast CT image G0 of the head of the patient from the image storage server 3. Moreover, the information acquisition unit 21 acquires the training data for training a neural network from the image storage server 3 in order to construct the discriminative model described below.

The information derivation unit 22 derives an infarction region and a large vessel occlusion part in the CT image G0. The infarction region and the large vessel occlusion part are examples of a first disease region and a second disease region according to the present disclosure, respectively. Specifically, the information derivation unit 22 derives the large vessel occlusion part in the CT image G0 based on the CT image G0 and the infarction region, and updates the infarction region in the CT image G0 based on the CT image G0 and the derived large vessel occlusion part. Further, the information derivation unit 22 updates the large vessel occlusion part based on the CT image G0 and the updated infarction region. Then, the information derivation unit 22 repeats the update of the infarction region and the update of the large vessel occlusion part until a predetermined end condition is satisfied, and derives the infarction region and the large vessel occlusion part in a case in which the predetermined end condition is satisfied, as final infarction region and large vessel occlusion part.

Figure 4:
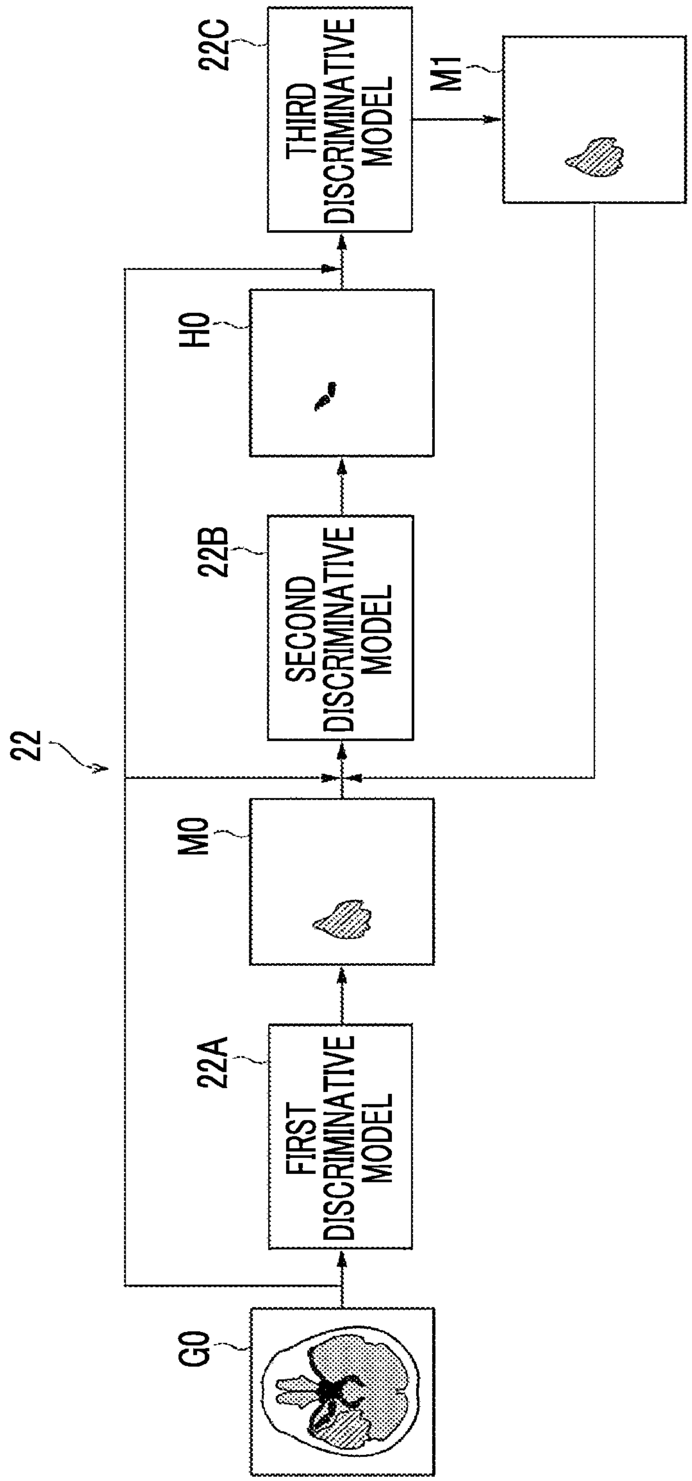
FIG. 4 is a schematic block diagram showing a configuration of an information derivation unit in the first embodiment.

FIG. 4 is a schematic block diagram showing a configuration of the information derivation unit 22. As shown in FIG. 4, the information derivation unit 22 includes a first discriminative model 22A, a second discriminative model 22B, and a third discriminative model 22C. The first discriminative model 22A is constructed by subjecting a convolutional neural network (CNN) to machine learning to extract the infarction region of the brain as the first disease region from the CT image G0 which is a processing target. For the construction of the first discriminative model 22A, for example, the method disclosed in JP2020-054580A can be used. Specifically, the first discriminative model 22A can be constructed by subjecting the CNN to machine learning using the non-contrast CT image of the head and a mask image representing the infarction region in the non-contrast CT image as the training data. As a result, the first discriminative model 22A extracts the infarction region in the CT image G0 from the CT image G0 and outputs a mask image M0 representing the infarction region in the CT image G0.

The second discriminative model 22B is constructed by subjecting U-Net, which is a type of the convolutional neural network, to machine learning using a large amount of the training data to extract the large vessel occlusion part from the CT image G0 as the second disease region based on the CT image G0 and the mask image M0 representing the infarction region in the CT image G0.

The third discriminative model 22C is constructed by subjecting U-Net, which is a type of the convolutional neural network, to machine learning using a large amount of the training data to extract the infarction region from the CT image G0 as the updated first disease region based on the CT image G0 and a mask image H0 representing the large vessel occlusion part in the CT image G0.

Figure 5:
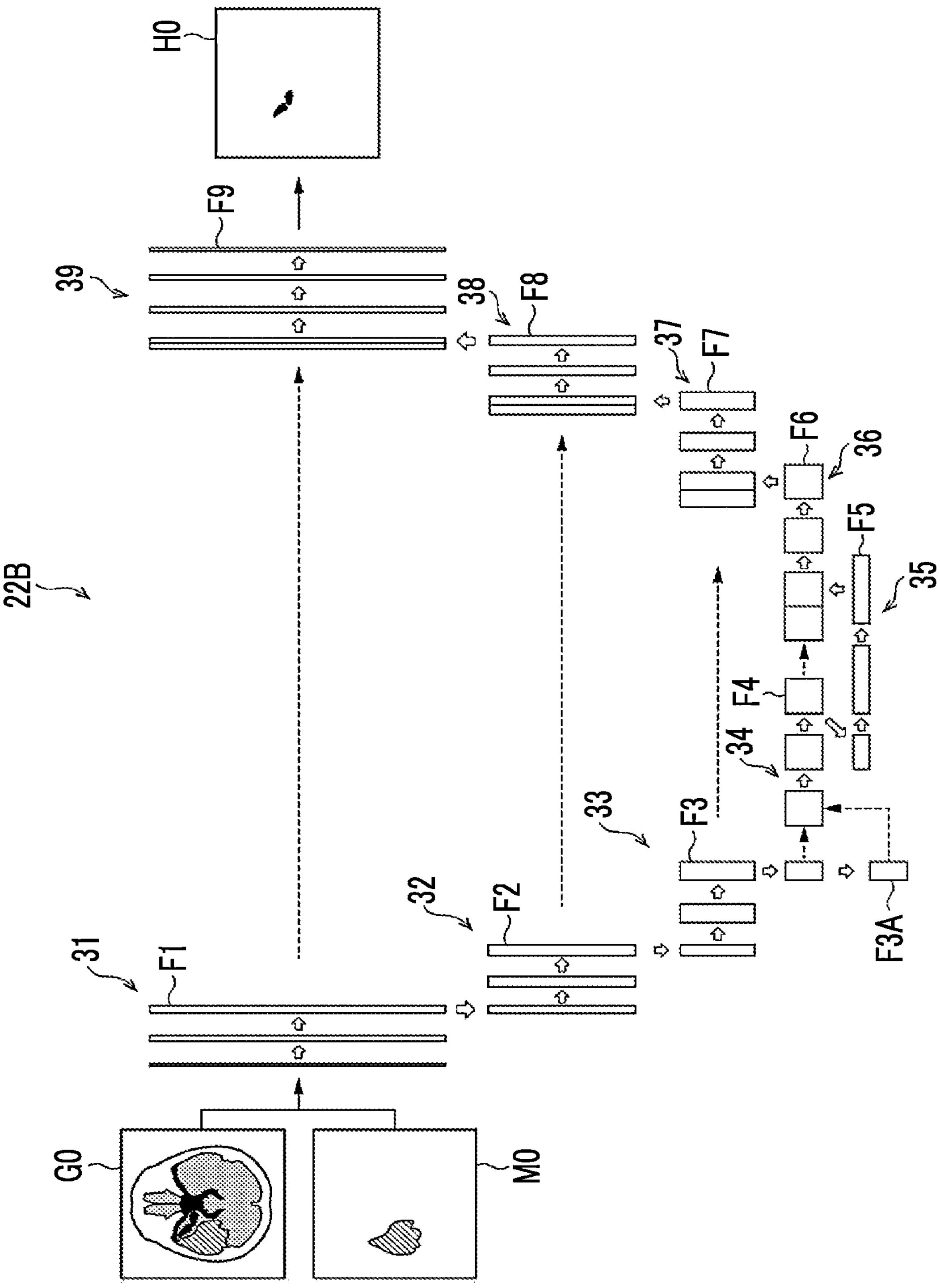
FIG. 5 is a diagram schematically showing a configuration of U-Net.

FIG. 5 is a diagram schematically showing a configuration of the U-Net. It should be noted that, although the U-Net for constructing the second discriminative model 22B will be described here, the U-Net for constructing the third discriminative model 22C also has the same configuration except that the input and output are different. As shown in FIG. 5, the second discriminative model 22B is configured by 9 layers of a first layer 31 to a ninth layer 39. It should be noted that, in the present embodiment, in a case of deriving the second disease region, information of regions symmetrical with respect to a midline of the brain in the CT image G0 and the mask image M0 representing the infarction region is used. The information of the regions symmetrical with respect to the midline of the brain will be described below.

In the present embodiment, the CT image G0 and the mask image M0 representing the infarction region in the CT image G0 are bonded to each other and are input to the first layer 31. It should be noted that, depending on the CT image G0, there is a case in which the midline of the brain is inclined with respect to a perpendicular bisector of the CT image G0 in the image. In such a case, it is preferable to rotate the brain in the CT image G0 such that the midline of the brain matches the perpendicular bisector of the CT image G0. Moreover, the center of the brain may deviate from the center of the CT image G0. In such a case, it is preferable to move the brain in the CT image G0 in parallel such that the center of the brain matches the center of the CT image G0. In this case, it is necessary to perform the rotation processing and/or parallel movement processing on the mask image M0 in the same manner.

The first layer 31 includes two convolutional layers, and outputs a feature amount map F1 in which two feature amount maps of the CT image G0 and the mask image M0 after the convolution are integrated. The integrated feature amount map F1 is input to the ninth layer 39 as shown by a broken line in FIG. 5. Moreover, the integrated feature amount map F1 is subjected to pooling, is reduced in size to ½, and is input to the second layer 32. In FIG. 5, the pooling is indicated by a downward arrow. It is assumed that, in a case of the convolution, for example, a 3×3 kernel is used in the present embodiment, but the present disclosure is not limited to this. Moreover, it is assumed that, in the pooling, the maximum value of the four pixels is adopted, but the present disclosure is not limited to this.

The second layer 32 includes two convolutional layers, and a feature amount map F2 output from the second layer 32 is input to the eighth layer 38 as shown by a broken line in FIG. 5. Moreover, the feature amount map F2 is subjected to pooling, is reduced in size to ½, and is input to the third layer 33.

The third layer 33 also includes two convolutional layers, and a feature amount map F3 output from the third layer 33 is input to the seventh layer 37 as shown by a broken line in FIG. 5. Moreover, the feature amount map F3 is subjected to pooling, is reduced in size to ½, and is input to the fourth layer 34.

Figure 6:
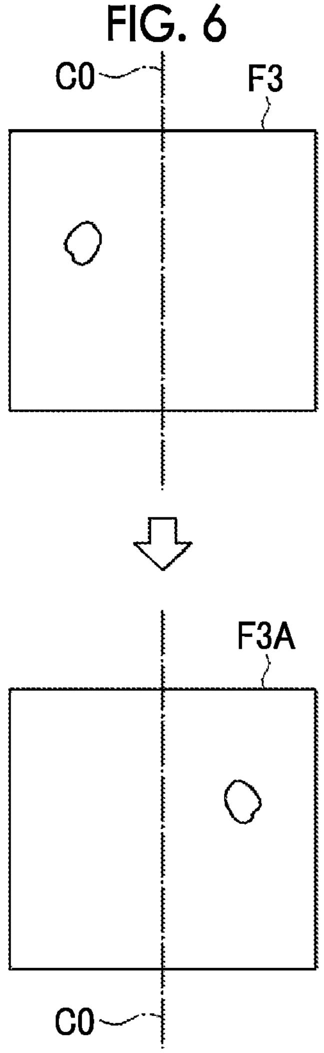
FIG. 6 is a diagram for describing reversal of a feature amount map.

Moreover, in the present embodiment, in a case of deriving the second disease region, the information of the regions symmetrical with respect to the midline of the brain in the CT image G0 and the mask image M0 representing the infarction region is used. Therefore, in the third layer 33 of the second discriminative model 22B, the feature amount map F3 subjected to the pooling is reversed left and right with respect to the midline of the brain, and a reversal feature amount map F3A is derived. The reversal feature amount map F3A is an example of reversal information according to the present disclosure. FIG. 6 is a diagram for describing the reversal of the feature amount map. As shown in FIG. 6, the feature amount map F3 is reversed left and right with respect to a midline CO of the brain, and the reversal feature amount map F3A is derived. It should be noted that, in the present embodiment, the reversal information is generated inside the U-Net. However, at a point in time at which the CT image G0 and the mask image M0 are input to the first layer 31, a reversal image of at least the CT image G0 out of the CT image G0 and the mask image M0 may be generated, the CT image G0, the reversal image of the CT image G0, and the mask image M0 are bonded to each other and are input to the first layer 31. Moreover, a reversal image of the mask image M0 may be generated in addition to the reversal image of the CT image G0, and the CT image G0, the reversal image of the CT image G0, the mask image M0, and the reversal image of the mask image M0 may be bonded to each other and are input to the first layer 31.

In this case, the reversal image need only be generated by rotating the brain in the CT image G0 such that the midline of the brain matches the perpendicular bisector of the CT image G0 or moving the brain in the CT image G0 in parallel such that the center of the brain matches the center of the CT image G0. Moreover, the rotation processing and/or the parallel movement processing need only also be performed on the mask image M0 as on the CT image G0.

The fourth layer 34 also includes two convolutional layers, and the feature amount map F3 subjected to the pooling and the reversal feature amount map F3A are input to the first convolutional layer. A feature amount map F4 output from the fourth layer 34 is input to the sixth layer 36 as shown by a broken line in FIG. 5. Moreover, the feature amount map F4 is subjected to pooling, is reduced in size to ½, and is input to the fifth layer 35.

The fifth layer 35 includes one convolutional layer, and a feature amount map F5 output from the fifth layer 35 is subjected to upsampling, is doubled in size, and is input to the sixth layer 36. In FIG. 5, the upsampling is indicated by an upward arrow.

The sixth layer 36 includes two convolutional layers, and performs a convolution operation by integrating the feature amount map F4 from the fourth layer 34 and the feature amount map F5, which is subjected to the upsampling, from the fifth layer 35. A feature amount map F6 output from the sixth layer 36 is subjected to upsampling, is doubled in size, and is input to the seventh layer 37.

The seventh layer 37 includes two convolutional layers, and performs the convolution operation by integrating the feature amount map F3 from the third layer 33 and the feature amount map F6, which is subjected to the upsampling, from the sixth layer 36. A feature amount map F7 output from the seventh layer 37 is subjected to upsampling and is input to the eighth layer 38.

The eighth layer 38 includes two convolutional layers, and performs the convolution operation by integrating the feature amount map F2 from the second layer 32 and the feature amount map F7, which is subjected to the upsampling, from the seventh layer 37. A feature amount map F8 output from the eighth layer 38 is subjected to upsampling and is input to the ninth layer 39.

The ninth layer 39 includes three convolutional layers, and performs the convolution operation by integrating the feature amount map F1 from the first layer 31 and the feature amount map F8, which is subjected to the upsampling, from the eighth layer 38. A feature amount map F9 output from the ninth layer 39 is an image obtained by extracting the large vessel occlusion part in the CT image G0.

Figure 7:
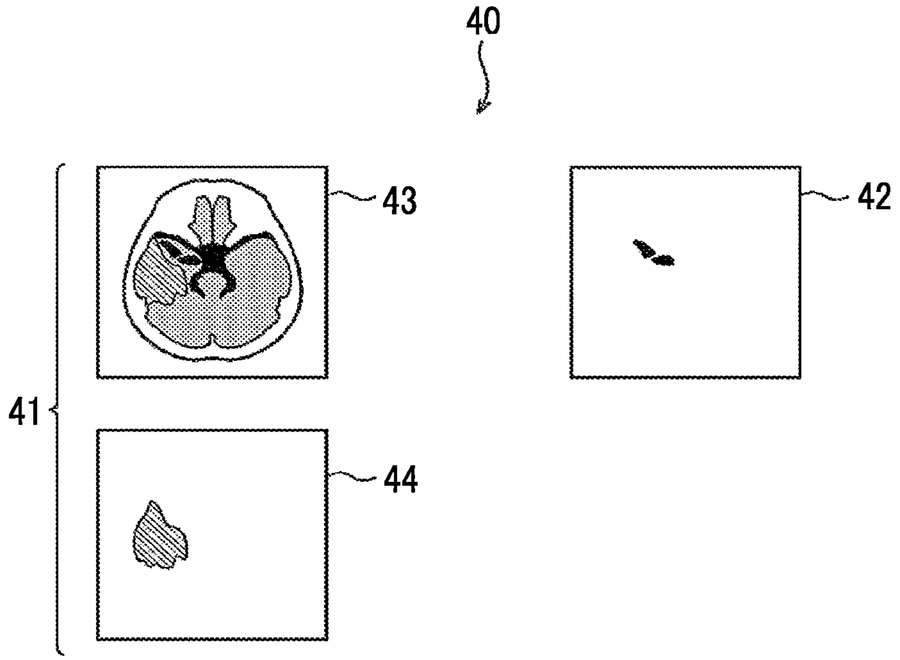
FIG. 7 is a diagram showing training data for training U-Net for constructing a second discriminative model in the first embodiment.

FIG. 7 is a diagram showing training data for training the U-Net for constructing the second discriminative model 22B in the first embodiment. As shown in FIG. 7, training data 40 consists of input data 41 and correct answer data 42. The input data 41 consists of a non-contrast CT image 43 and a mask image 44 representing the infarction region in the non-contrast CT image 43. The correct answer data 42 is a mask image representing the large vessel occlusion part in the non-contrast CT image 43.

In the present embodiment, a large amount of the training data 40 is stored in the image storage server 3, and the training data 40 is acquired from the image storage server 3 by the information acquisition unit 21 and is used for training the U-Net by the learning unit 23.

The learning unit 23 inputs the non-contrast CT image 43 and the mask image 44 which are the input data 41 to the U-Net for constructing the second discriminative model 22B, and outputs the image representing the large vessel occlusion part in the non-contrast CT image 43 from the U-Net. Specifically, the learning unit 23 extracts the large vessel occlusion part in the non-contrast CT image 43 by the U-Net, and outputs the mask image in which a portion of the large vessel occlusion part is masked. The learning unit 23 derives a difference between the output image and the correct answer data 42 as a loss, and learns the weight of the bonding of each layer in the U-Net and a coefficient of kernel such that the loss is small. It should be noted that, in a case of the learning, a perturbation may be added to the mask image 44. As the perturbation, for example, morphology processing may be added to the mask with a random probability, or the mask may be subjected to zero padding. By adding the perturbation to the mask image 44, it is possible to handle a pattern observed in a case of the cerebral infarction in a hyperacute phase in which only the thrombus appears on the image without a remarkable infarction region, and it is further possible to prevent the second discriminative model 22B being excessively dependent on the input mask image in a case of the discrimination.

Then, the learning unit 23 repeatedly performs the learning until the loss is equal to or less than a predetermined threshold value. As a result, in a case in which the non-contrast CT image G0 and the mask image M0 representing the infarction region in and the CT image G0 are input, the large vessel occlusion part included in the CT image G0 is extracted as the second disease region to construct the second discriminative model 22B that outputs the mask image H0 representing the large vessel occlusion part in the CT image G0. It should be noted that the learning unit 23 may construct the second discriminative model 22B by repeatedly performing the learning a predetermined number of times.

Figure 8:
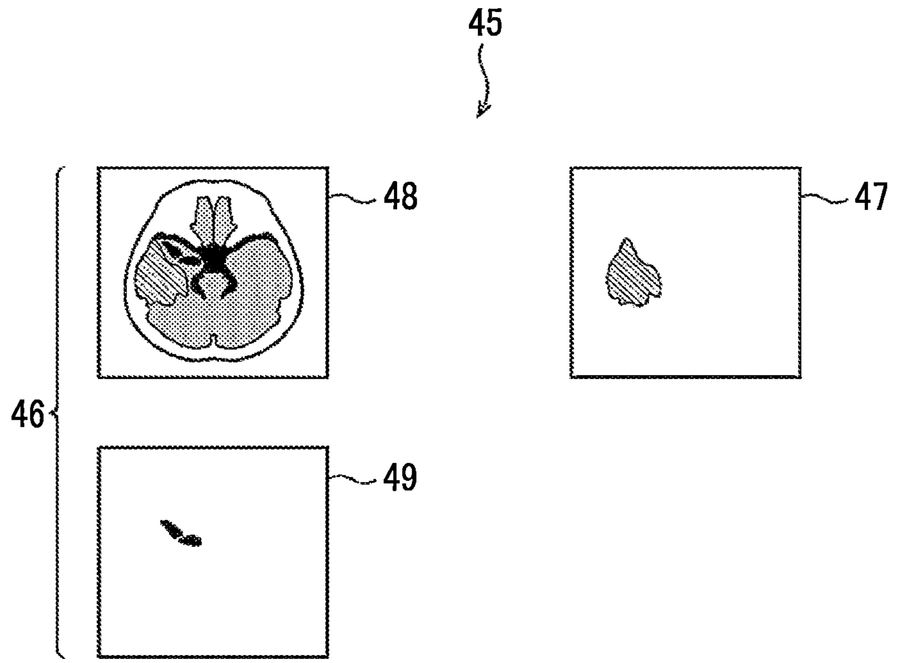
FIG. 8 is a diagram showing training data for training U-Net for constructing a third discriminative model in the first embodiment.

FIG. 8 is a diagram showing training data for training the U-Net for constructing the third discriminative model 22C in the first embodiment. As shown in FIG. 8, training data 45 consists of input data 46 and correct answer data 47. The input data 46 consists of a non-contrast CT image 48 and a mask image 49 representing the large vessel occlusion part in the non-contrast CT image 48. The correct answer data 47 is a mask image representing the infarction region in the non-contrast CT image 48.

The learning unit 23 inputs the non-contrast CT image 48 and the mask image 49 which are the input data 46 to the U-Net for constructing the third discriminative model 22C, and outputs the image representing the infarction region in the non-contrast CT image 48 from the U-Net. Specifically, the learning unit 23 extracts the infarction region in the non-contrast CT image 48 by the U-Net, and outputs the mask image in which a portion of the infarction region is masked. The learning unit 23 derives a difference between the output image and the correct answer data 47 as a loss, and learns the weight of the bonding of each layer in the U-Net and the coefficient of kernel such that the loss is small. It should be noted that, in a case of the learning, a perturbation may be added to the mask image 49. As the perturbation, for example, morphology processing may be added to the mask with a random probability, or the mask may be subjected to zero padding. By adding the perturbation to the mask image 49, it is possible to handle a pattern in which a remarkable thrombus does not appear on the image (for example, in a case of atherosclerotic cerebral infarction), and it is further possible to prevent the third discriminative model 22C being excessively dependent on the input mask image in a case of the discrimination.

Then, the learning unit 23 repeatedly performs the learning until the loss is equal to or less than a predetermined threshold value. As a result, in a case in which the non-contrast CT image G0 and the mask image H0 representing the large vessel occlusion part in and the CT image G0 are input, the infarction region included in the CT image G0 is extracted as the second disease region to construct the third discriminative model 22C that outputs a mask image M1 representing the infarction region in the CT image G0. It should be noted that the learning unit 23 may construct the third discriminative model 22C by repeatedly performing the learning a predetermined number of times.

It should be noted that the configurations of the U-Nets constituting the second discriminative model 22B and the third discriminative model 22C are not limited to those shown in FIG. 5. For example, in the U-Net shown in FIG. 5, the reversal feature amount map F3A is derived from the feature amount map F3 output from the third layer 33, but the reversal feature amount map may be used in any layer in the U-Net. Moreover, the number of convolutional layers of each layer in the U-Net is not limited to that shown in FIG. 5.

The information derivation unit 22 inputs the CT image G0 and the mask image M0 representing the infarction region derived by the first discriminative model 22A to the second discriminative model 22B constructed as described above. Then, the information derivation unit 22 causes the second discriminative model 22B to extract the large vessel occlusion part in the CT image G0 and output the mask image H0 representing the large vessel occlusion part. Moreover, the information derivation unit 22 inputs the CT image G0 and the mask image H0 representing the large vessel occlusion part to the third discriminative model 22C. Then, the information derivation unit 22 causes the third discriminative model 22C to extract the updated infarction region in the CT image G0 and output the mask image M1 representing the updated infarction region.

Moreover, the information derivation unit 22 inputs the CT image G0 and the mask image M1 representing the updated infarction region to the second discriminative model 22B. Then, the information derivation unit 22 causes the second discriminative model 22B to extract the updated large vessel occlusion part in the CT image G0 and output a mask image H1 representing the updated large vessel occlusion part, thereby updating the large vessel occlusion part. Further, the information derivation unit 22 repeats the update of the infarction region and the update of the large vessel occlusion part until the predetermined end condition is satisfied, and derives the infarction region and the large vessel occlusion part in a case in which the predetermined end condition is satisfied, as final infarction region and large vessel occlusion part.

It should be noted that the end condition need only be a condition in which the update of the infarction region and the update of the large vessel occlusion part are repeated a predetermined number of times. Moreover, the end condition may be a condition in which at least one of a difference between the updated infarction region and the infarction region immediately before the update or a difference between the updated large vessel occlusion part and the large vessel occlusion part immediately before the update is equal to or less than a predetermined threshold value. Here, as the differences, a correlation value between the updated infarction region and the infarction region immediately before the update on the CT image G0 and a correlation value between the updated large vessel occlusion part and the large vessel occlusion part immediately before the updated need only be used.

The quantitative value derivation unit 24 derives a quantitative value for at least one of the infarction region or the large vessel occlusion part derived by the information derivation unit 22. The quantitative value is an example of quantitative information in the present disclosure. In the present embodiment, it is assumed that the quantitative value derivation unit 24 derives the quantitative values of both the infarction region and the large vessel occlusion part, but the quantitative value of any one of the infarction region or the large vessel occlusion part may be derived. Since the CT image G0 is the three-dimensional image, the quantitative value derivation unit 24 may derive a volume of the infarction region, a volume of the large vessel occlusion part, and a length of the large vessel occlusion part as the quantitative values. Moreover, the quantitative value derivation unit 24 may derive a score of ASPECTS as the quantitative value.

The "ASPECTS" is an abbreviation for alberta stroke program early CT score, and is a scoring method in which an early CT sign of a simple CT is quantified for the cerebral infarction in a middle cerebral artery region. Specifically, the ASPECTS is a method in which, in a case in which the medical image is the CT image, the middle cerebral artery region is classified into 10 regions in two representative cross sections (basal ganglia level and radiation coronary level), the presence or absence of early ischemic change in each region is evaluated, and a positive part is scored by a point-deduction method. In the ASPECTS, an area of the infarction region is larger as the score is lower. The quantitative value derivation unit 24 need only derive the score depending on whether or not the infarction region is included in the 10 regions described above.

Figure 9:
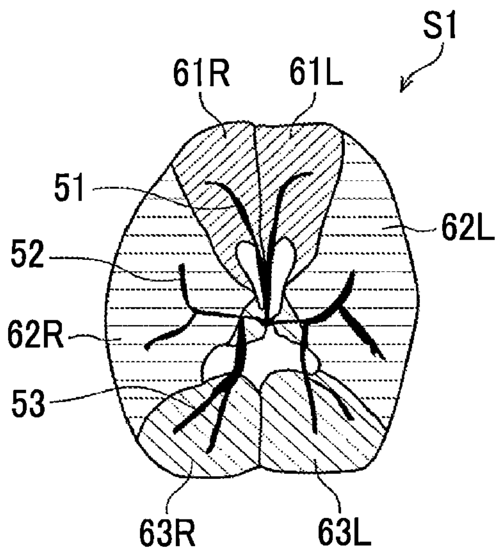
FIG. 9 is a diagram showing an artery and a dominant region in the brain.

Moreover, the quantitative value derivation unit 24 may specify a dominant region of the occluded blood vessel based on the large vessel occlusion part, and derive an overlapping amount (volume) between the dominant region and the infarction region as the quantitative value. FIG. 9 is a diagram showing an artery and a dominant region in the brain. It should be noted that FIG. 9 shows a slice image 51 on a certain tomographic plane of the CT image G0. As shown in FIG. 9, the brain includes an anterior cerebral artery (ACA) 51, a middle cerebral artery (MCA) 52, and a posterior cerebral artery (PCA) 53. Moreover, although not shown, an internal carotid artery (ICA) is also included. The brain is divided into middle cerebral artery dominant regions 62L and 62R, left and right anterior cerebral artery dominant regions 61L and 61R, and posterior cerebral artery dominant regions 63L and 63R in which the blood flows are dominated by the anterior cerebral artery 51, the middle cerebral artery 52, and the posterior cerebral artery 53, respectively. It should be noted that, in FIG. 9, a right side on the paper surface is a region on a left side of the brain.

It should be noted that the dominant region need only be specified by the registration of the CT image G0 with a prepared standard brain image in which the dominant region is specified.

The quantitative value derivation unit 24 specifies the artery in which the large vessel occlusion part is present, and specifies the dominant region by the specified artery of the brain. For example, in a case in which the large vessel occlusion part is present in the left anterior cerebral artery, the dominant region is specified as the anterior cerebral artery dominant region 61L. Here, the infarction region is generated downstream of the part in which the thrombus is present in the artery. Therefore, the infarction region is present in the anterior cerebral artery dominant region 61L. Therefore, the quantitative value derivation unit 24 need only derive the volume of the infarction region with respect to the volume of the anterior cerebral artery dominant region 61L in the CT image G0 as the quantitative value.

Figure 10:
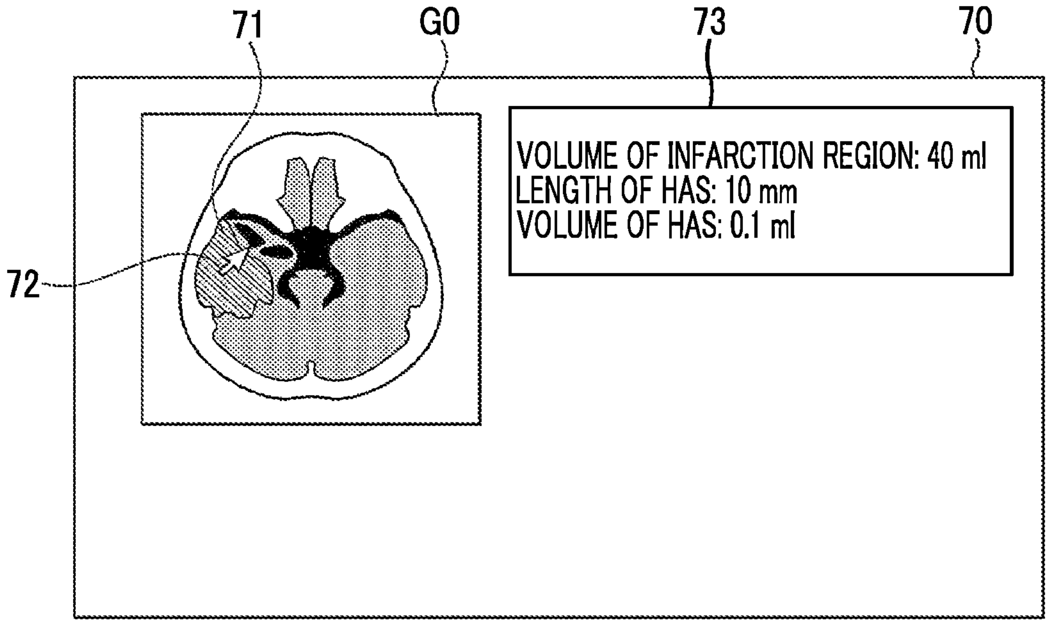
FIG. 10 is a diagram showing a display screen.

The display controller 25 displays the CT image G0 of the patient and the quantitative value on the display 14. FIG. 10 is a diagram showing a display screen. As shown in FIG. 10, a slice image included in the CT image G0 of the patient is displayed on a display screen 70 in a switchable manner based on an operation of the input device 15. Moreover, a mask 71 of the infarction region is superimposed and displayed on the CT image G0. Moreover, an arrow-shaped mark 72 indicating the large vessel occlusion part is also superimposed and displayed. Moreover, on the right side of the CT image G0, a quantitative value 73 derived by the quantitative value derivation unit 24 is displayed. Specifically, the volume of the infarction region (40 ml), the length of the large vessel occlusion part (length of HAS: 10 mm), and the volume of the large vessel occlusion part (volume of HAS: 0.1 ml) are displayed.

Figure 11:
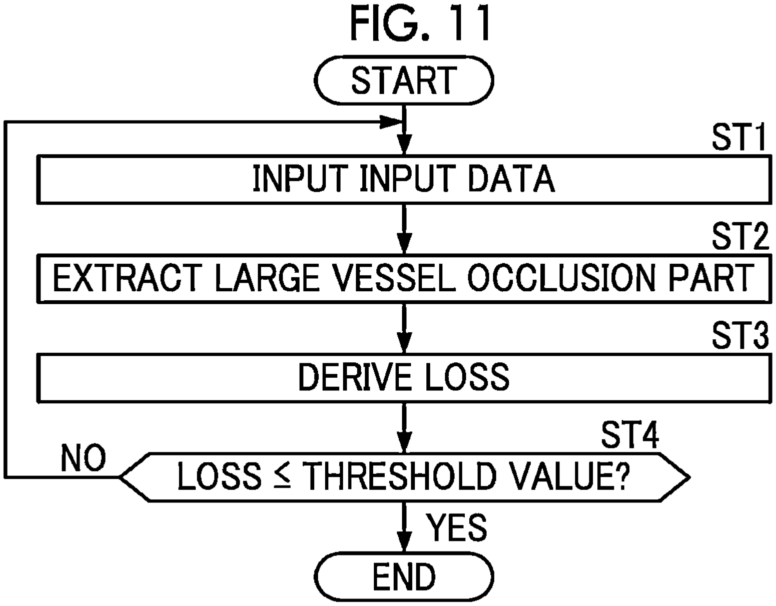
FIG. 11 is a flowchart showing learning processing performed in the first embodiment.

Next, processing performed in the first embodiment will be described. FIG. 11 is a flowchart showing learning processing performed in the first embodiment. It should be noted that it is assumed that the training data is acquired from the image storage server 3 and stored in the storage 13. Moreover, training the U-Net for constructing the second discriminative model 22B will be described here. First, the learning unit 23 inputs the input data 41 included in the training data 40 to the U-Net (step ST1), and causes the U-Net to extract the large vessel occlusion part (step ST2). Then, the learning unit 23 derives the loss from the extracted large vessel occlusion part and the correct answer data 42 (step ST3), and determines whether or not the loss is equal to or less than the predetermined threshold value (step ST4).

In a case in which a negative determination is made in step ST4, the processing returns to step ST1, and the learning unit 23 repeats the processing of step ST1 to step ST4. In a case in which a positive determination is made in step ST4, the processing ends. As a result, the second discriminative model 22B is constructed. It should be noted that training the U-Net for constructing the third discriminative model 22C need only be performed as in training the U-Net for constructing the second discriminative model 22B.

Figure 12:
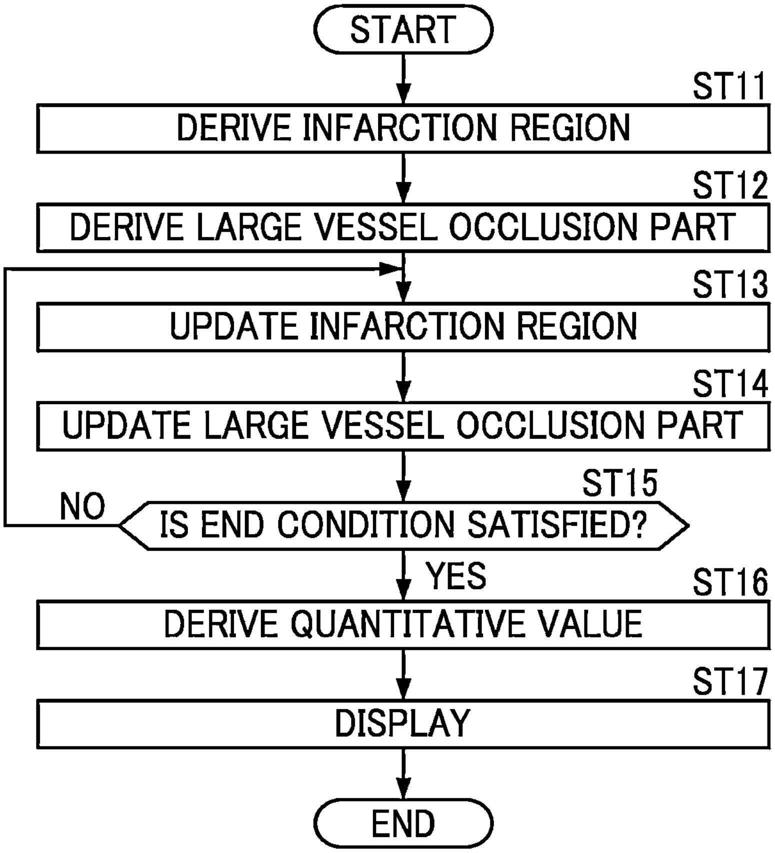
FIG. 12 is a flowchart showing information processing performed in the first embodiment.

FIG. 12 is a flowchart showing information processing performed in the first embodiment. It should be noted that it is assumed that the non-contrast CT image G0 which is the processing target is acquired from the image storage server 3 and stored in the storage 13. First, the information derivation unit 22 derives the infarction region in the CT image G0 using the first discriminative model 22A (step ST11). Moreover, the information derivation unit 22 derives the large vessel occlusion part in the CT image G0 based on the CT image G0 and the mask image M0 representing the infarction region using the second discriminative model 22B (step ST12).

Next, the information derivation unit 22 derives the updated infarction region in the CT image G0 based on the CT image G0 and the mask image H0 representing the derived large vessel occlusion part using the third discriminative model 22C (update the infarction region; step ST13). Further, the information derivation unit 22 derives the updated large vessel occlusion part in the CT image G0 based on the CT image G0 and the mask image representing the updated infarction region using the second discriminative model 22B (update the large vessel occlusion part; step ST14).

The information derivation unit 22 determines whether or not the end condition is satisfied (step ST15), returns to step ST13 in a case in which a negative determination is made in step ST15, and repeats the update of the infarction region and the update of the large vessel occlusion part. In a case in which a positive determination is made in step ST15, the quantitative value derivation unit 24 derives the quantitative value based on the information of the infarction region and the large vessel occlusion part (step ST16). Then, the display controller 25 displays the CT image G0 and the quantitative value (step ST17), and ends the processing.

As described above, in the first embodiment, the large vessel occlusion part in the CT image G0 is derived based on the non-contrast CT image G0 of the head of the patient and the infarction region in the CT image G0. As a result, since the infarction region can be considered, the large vessel occlusion part can be accurately specified in the CT image G0. Moreover, in the first embodiment, the infarction region in the CT image G0 is derived based on the non-contrast CT image G0 of the head of the patient and the large vessel occlusion part in the CT image G0. As a result, since the large vessel occlusion part can be considered, the infarction region can be accurately specified in the CT image G0. Moreover, in the first embodiment, since the infarction region and the large vessel occlusion part are repeatedly updated until the end condition is satisfied, the infarction region and the large vessel occlusion part can be more accurately specified.

Here, a brain disease, such as the cerebral infarction, is rarely developed simultaneously in both the left brain and the right brain. Therefore, by using the reversal feature amount map F3A in which the feature amount map F3 is reversed with respect to the midline CO of the brain, it is possible to specify the infarction region and the large vessel occlusion part while comparing the features of the left and right brains. As a result, the infarction region and the large vessel occlusion part can be accurately specified.

Moreover, by displaying the quantitative value, a doctor can easily decide the treatment policy based on the quantitative value. For example, by displaying the volume or the length of the large vessel occlusion part, it is easy to decide a type or a length of a device used in the application of thrombectomy treatment method.

Next, a second embodiment of the present disclosure will be described. It should be noted that a configuration of an information processing apparatus in the second embodiment is the same as the configuration of the information processing apparatus in the first embodiment, only the processing to be performed is different, and thus the detailed description of the apparatus will be omitted.

Figure 13:
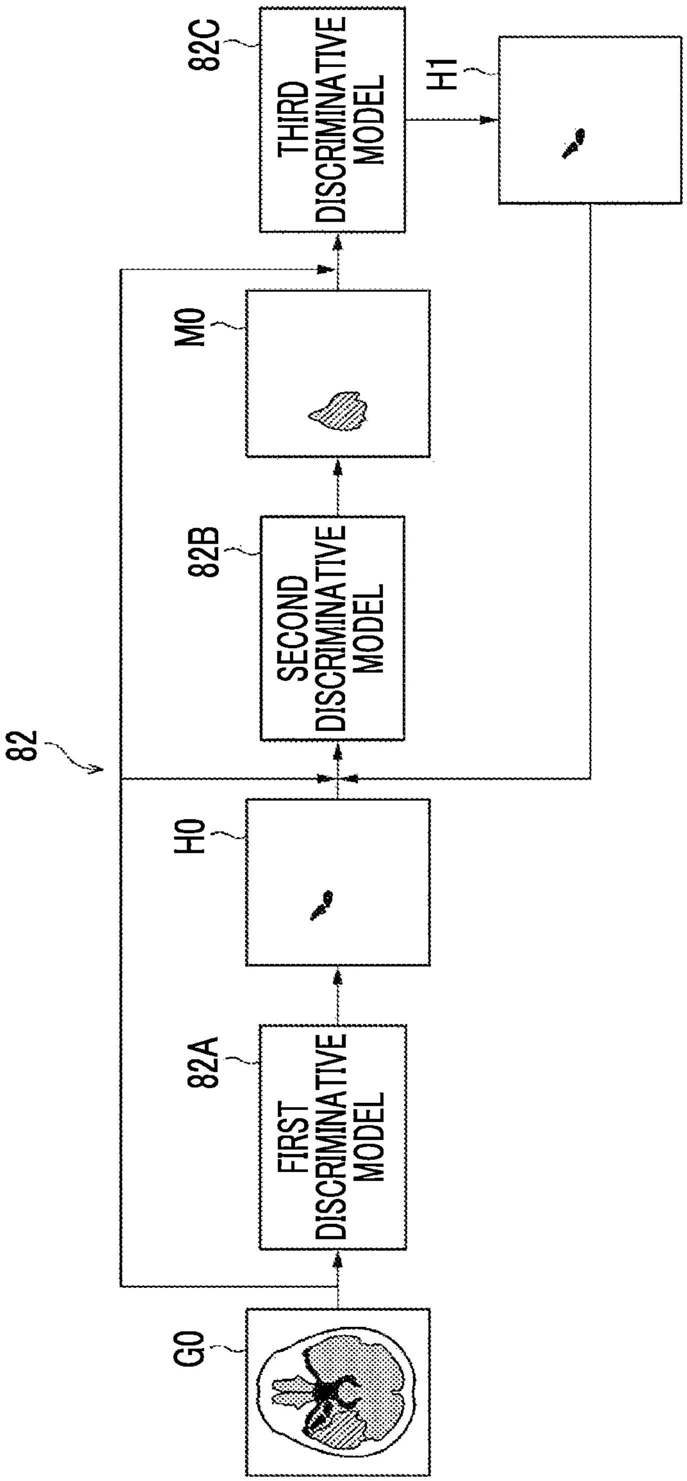
FIG. 13 is a schematic block diagram showing a configuration of an information derivation unit in a second embodiment.

FIG. 13 is a schematic block diagram showing the configuration of an information derivation unit 82 in the second embodiment. As shown in FIG. 13, the information derivation unit 82 according to the second embodiment includes a first discriminative model 82A, a second discriminative model 82B, and a third discriminative model 82C. The first discriminative model 82A in the second embodiment is constructed by subjecting the CNN to machine learning to extract the large vessel occlusion part from the CT image G0 as the first disease region. For the construction of the first discriminative model 82A, for example, the method disclosed in JP2020-054580A can be used. Specifically, the first discriminative model 82A can be constructed by subjecting the CNN to machine learning using the large vessel occlusion part in the non-contrast CT image and the non-contrast CT image of the head as the training data.

Similar to the third discriminative model 22C in the first embodiment, the second discriminative model 82B in the second embodiment is constructed by subjecting the U-Net, which is a type of the convolutional neural network, to machine learning using a large amount of the training data to extract the infarction region from the CT image G0 as the second disease region based on the CT image G0 and the mask image H0 representing the large vessel occlusion part in the CT image G0.

Similar to the second discriminative model 22B in the first embodiment, the third discriminative model 82C in the second embodiment is constructed by subjecting U-Net, which is a type of the convolutional neural network, to machine learning using a large amount of the training data to extract the large vessel occlusion part from the CT image G0 as the updated first disease region based on the CT image G0 and the mask image M0 representing the infarction region in the CT image G0.

In the second embodiment, the information derivation unit 82 inputs the CT image G0 and the mask image H0 representing the large vessel occlusion part derived by the first discriminative model 82A to the second discriminative model 82B. Then, the information derivation unit 82 causes the second discriminative model 82B to extract the infarction region in the CT image G0 and output the mask image M0 representing the infarction region. Moreover, the information derivation unit 82 inputs the CT image G0 and the mask image M0 representing the infarction region to the third discriminative model 82C. Then, the information derivation unit 82 causes the third discriminative model 82C to extract the updated large vessel occlusion part in the CT image G0 and output the mask image H1 representing the updated large vessel occlusion part.

Moreover, the information derivation unit 82 inputs the CT image G0 and the mask image H1 representing the updated large vessel occlusion part to the second discriminative model 82B. Then, the information derivation unit 82 updates the infarction region by causing the second discriminative model 82B to extract the updated infarction region in the CT image G0 and output the mask image M1 representing the updated infarction region. Further, the information derivation unit 82 repeats the update of the infarction region and the update of the large vessel occlusion part until the predetermined end condition is satisfied, and derives the infarction region and the large vessel occlusion part in a case in which the predetermined end condition is satisfied, as final infarction region and large vessel occlusion part.

It should be noted that the end condition need only be a condition in which the update of the infarction region and the update of the large vessel occlusion part are repeated a predetermined number of times, as in the first embodiment. Moreover, the end condition may be a condition in which at least one of a difference between the updated infarction region and the infarction region immediately before the update or a difference between the updated large vessel occlusion part and the large vessel occlusion part immediately before the update is equal to or less than a predetermined threshold value. Here, as the differences, a correlation value between the updated infarction region and the infarction region immediately before the update on the CT image G0 and a correlation value between the updated large vessel occlusion part and the large vessel occlusion part immediately before the updated need only be used.

Next, processing performed in the second embodiment will be described. It should be noted that training the U-Nets for constructing the second discriminative model 82B and the third discriminative model 82C of the information derivation unit 82 in the second embodiment is performed as in the first embodiment, and thus the description of the learning processing will be omitted here.

Figure 14:
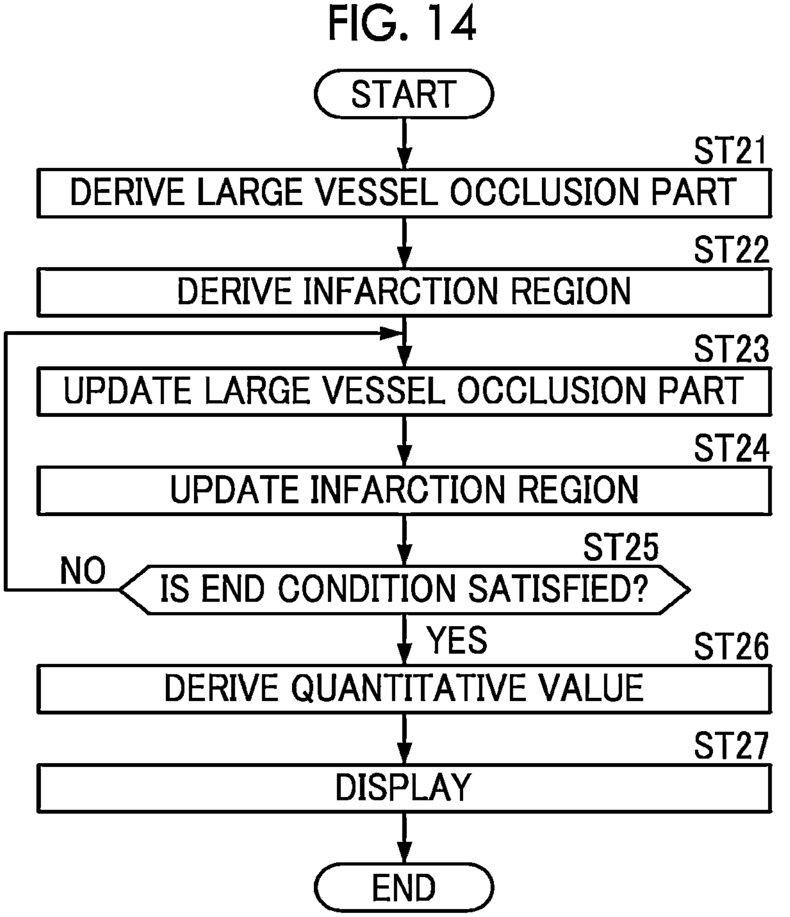
FIG. 14 is a flowchart showing information processing performed in the second embodiment.

FIG. 14 is a flowchart showing information processing performed in the second embodiment. It should be noted that it is assumed that the non-contrast CT image G0 which is the processing target is acquired from the image storage server 3 and stored in the storage 13. First, the information derivation unit 82 derives the large vessel occlusion part in the CT image G0 using the first discriminative model 82A (step ST21). Moreover, the information derivation unit 82 derives the infarction region in the CT image G0 based on the CT image G0 and the mask image H0 representing the large vessel occlusion part using the second discriminative model 82B (step ST22).

Next, the information derivation unit 82 derives the updated large vessel occlusion part in the CT image G0 based on the CT image G0 and the mask image M0 representing the derived infarction region using the third discriminative model 82C (update the large vessel occlusion part; step ST23). Further, the information derivation unit 82 derives the updated infarction region in the CT image G0 based on the CT image G0 and the mask image representing the updated large vessel occlusion part using the second discriminative model 82B (update the infarction region; step ST24).

The information derivation unit 82 determines whether or not the end condition is satisfied (step ST25), returns to step ST23 in a case in which a negative determination is made in step ST25, and repeats the update of the large vessel occlusion part and the update of the infarction region. In a case in which a positive determination is made in step ST25, the quantitative value derivation unit 24 derives the quantitative value based on the information of the infarction region and the large vessel occlusion part (step ST26). Then, the display controller 25 displays the CT image G0 and the quantitative value (step ST27), and ends the processing.

Next, a third embodiment of the present disclosure will be described. It should be noted that a configuration of an information processing apparatus in the third embodiment is the same as the configuration of the information processing apparatus in the first embodiment, only the processing to be performed is different, and thus the detailed description of the apparatus will be omitted.

Figure 15:
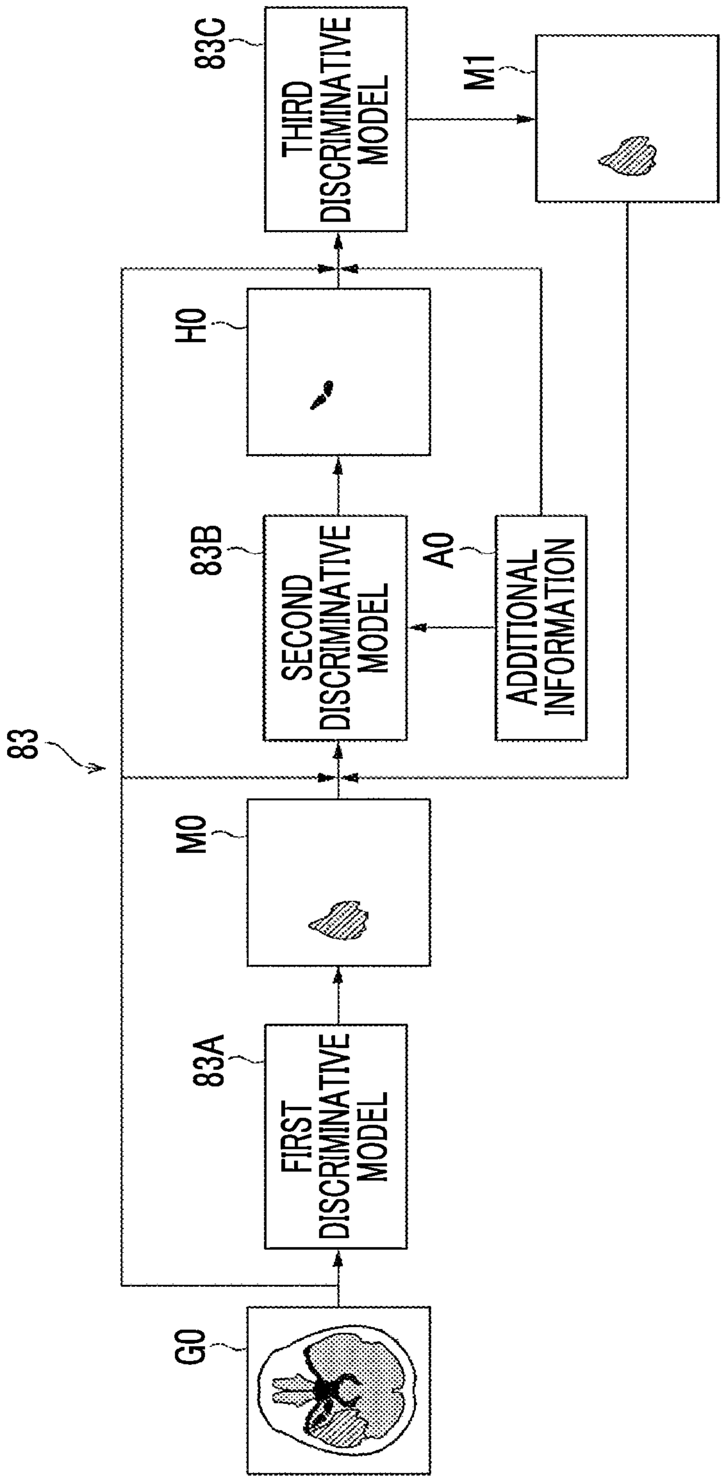
FIG. 15 is a schematic block diagram showing a configuration of an information derivation unit in a third embodiment.

FIG. 15 is a schematic block diagram showing a configuration of an information derivation unit in the third embodiment. As shown in FIG. 15, an information derivation unit 83 according to the third embodiment includes a first discriminative model 83A, a second discriminative model 83B, and a third discriminative model 83C. Similar to the first discriminative model 22A in the first embodiment, the first discriminative model 83A in the third embodiment is constructed by subjecting the CNN to machine learning to extract the infarction region from the CT image G0 as the first disease region.

The second discriminative model 83B in the third embodiment is constructed by subjecting the U-Net to machine learning using a large amount of the training data to extract the large vessel occlusion part from the CT image G0 as the second disease region based on information (hereinafter, referred to as additional information A0) of at least one of information representing an anatomical region of the brain or the clinical information, in addition to the CT image G0 and the mask image M0 representing the infarction region in the CT image G0. It should be noted that the configuration of the U-Net is the same as that of the first embodiment, and thus the detailed description thereof will be omitted here.

The third discriminative model 83C in the third embodiment is constructed by subjecting the U-Net to machine learning using a large amount of the training data to extract the infarction region from the CT image G0 as the updated first disease region based on the additional information A0, in addition to the CT image G0 and the mask image H0 representing the large vessel occlusion part in the CT image G0. It should be noted that the configuration of the U-Net is the same as that of the first embodiment, and thus the detailed description thereof will be omitted here.

Figure 16:
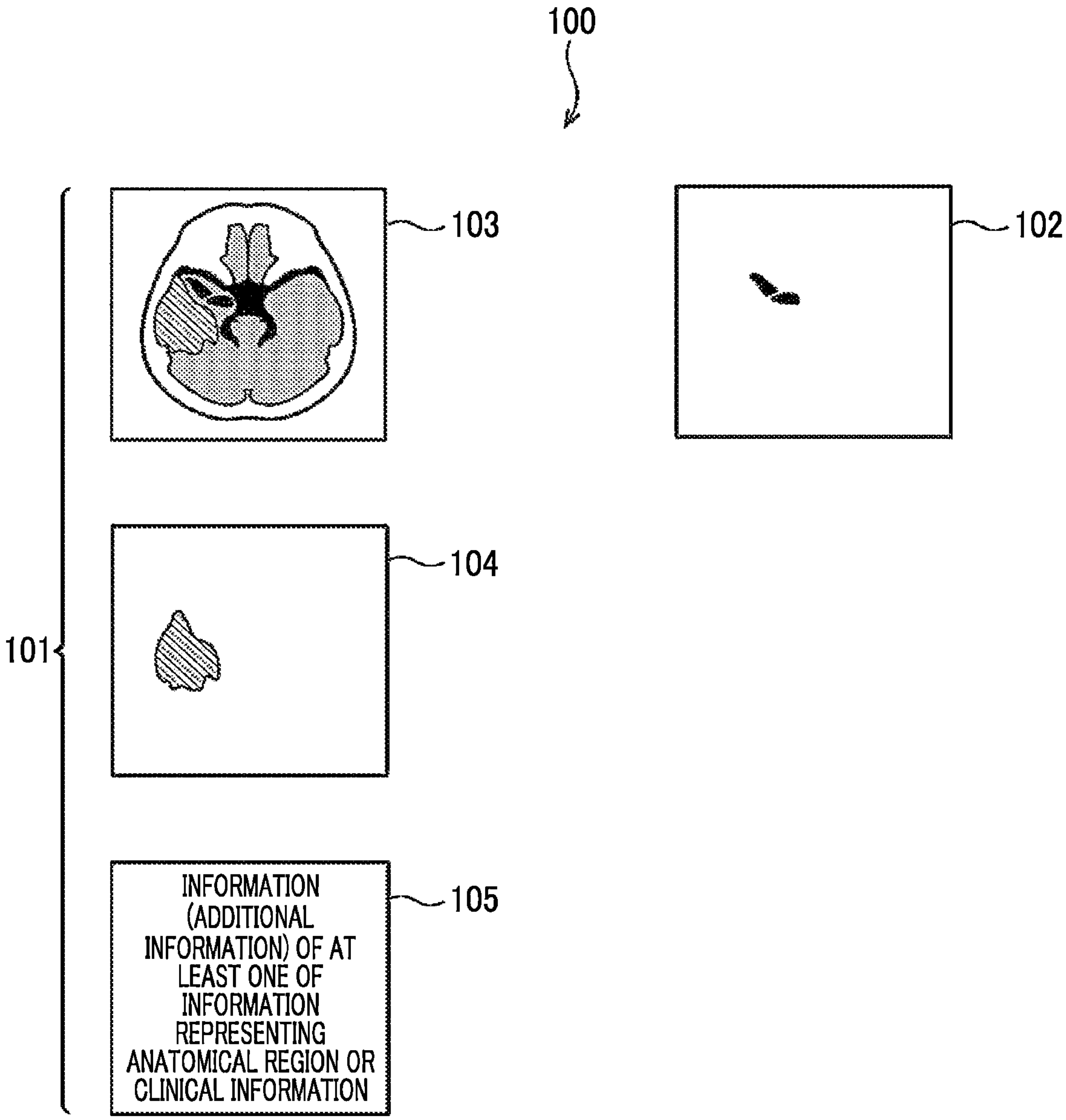
FIG. 16 is a diagram showing training data for training U-Net for constructing a second discriminative model in the third embodiment.

FIG. 16 is a diagram showing training data for training the U-Net for constructing the second discriminative model 83B in the third embodiment. As shown in FIG. 16, training data 100 consists of input data 101 and correct answer data 102. The input data 101 consists of a non-contrast CT image 103, a mask image 104 representing the infarction region in the non-contrast CT image 103, and information (referred to as additional information) 105 of at least one of the information representing the anatomical region or the clinical information. The correct answer data 102 is a mask image representing the large vessel occlusion part in the non-contrast CT image 103.

Here, as the information representing the anatomical region, for example, a mask image of the blood vessel dominant region in which the infarction region is present in the non-contrast CT image 103 can be used. Moreover, the mask image of the region of the ASPECTS in which the infarction region is present in the non-contrast CT image 103 can be used as the information representing the anatomical region. As the clinical information, a score of the ASPECTS for the non-contrast CT image 103 and a national institutes of health stroke scale (NIHSS) for the patient from whom the non-contrast CT image 103 is acquired can be used. The NIHSS is one of the most widely used evaluation methods in the world as an evaluation scale for the severity of stroke neurology.

In the third embodiment, the learning unit 23 constructs the second discriminative model 83B by training the U-Net using a large amount of the training data 100 shown in FIG. 16. As a result, the second discriminative model 83B in the third embodiment extracts the large vessel occlusion part from the CT image G0 and outputs the mask image H0 representing the large vessel occlusion part in a case in which the CT image G0, the mask image M0 representing the infarction region, and the additional information A0 are input.

Figure 17:
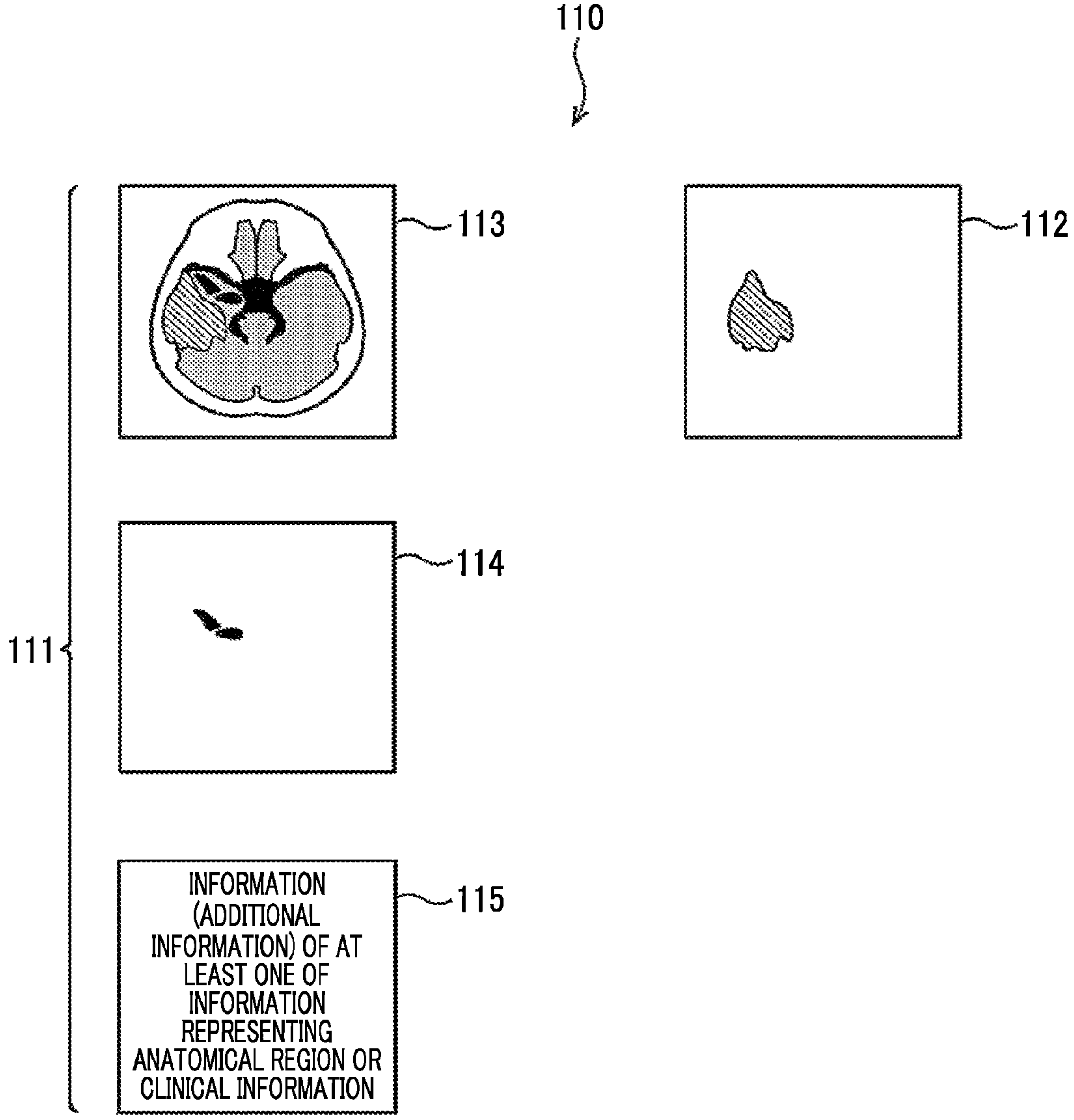
FIG. 17 is a diagram showing training data for training U-Net for constructing a third discriminative model in the third embodiment.

FIG. 17 is a diagram showing training data for training the U-Net for constructing the third discriminative model 83C in the third embodiment. As shown in FIG. 17, the training data 110 consists of input data 111 and correct answer data 112. The input data 111 consists of a non-contrast CT image 113, a mask image 114 representing the large vessel occlusion part in the non-contrast CT image 113, and information (referred to as additional information) 115 of at least one of the information representing the anatomical region or the clinical information. The correct answer data 112 is a mask image representing the infarction region in the non-contrast CT image 113.

In the third embodiment, the learning unit 23 constructs the third discriminative model 83C by training the U-Net using a large amount of the training data 110 shown in FIG. 17. As a result, the third discriminative model 83C in the third embodiment extracts the infarction region from the CT image G0 and outputs the mask image M0 representing the infarction region in a case in which the CT image G0, the mask image H0 representing the large vessel occlusion part, and the additional information A0 are input.

It should be noted that the learning processing in the third embodiment is different from that in the first embodiment only in that the additional information A0 is used, and thus the detailed description of the learning processing will be omitted. Moreover, the information processing in the third embodiment is different from that in the first embodiment only in that the information input to the second discriminative model 83B includes the additional information A0 of the patient in addition to the CT image G0 and the mask image representing the infarction region. Moreover, the information processing in the third embodiment is different from that in the first embodiment only in that the information input to the third discriminative model 83C includes the additional information A0 of the patient in addition to the CT image G0 and the mask image representing the large vessel occlusion part. Therefore, the detailed description of the information processing will be omitted.

In a third embodiment, the large vessel occlusion part in the CT image G0 is derived based on the additional information in addition to the non-contrast CT image G0 of the head of the patient and the infarction region in the and the CT image G0. As a result, the large vessel occlusion part can be more accurately specified in the CT image G0. Moreover, in the third embodiment, the infarction region in the CT image G0 is derived based on the additional information in addition to the non-contrast CT image G0 of the head of the patient and the large vessel occlusion part in the CT image G0. As a result, the infarction region can be more accurately specified in the CT image G0.

It should be noted that it is needless to say that, in the second embodiment, the second discriminative model 82B and the third discriminative model 82C may be constructed by using the additional information as in the third embodiment.

Moreover, in each of the embodiments described above, in the second discriminative model and the third discriminative model, the infarction region and the large vessel occlusion part are derived by using the information of the regions symmetrical with respect to the midline of the brain in the CT image G0, the first disease region, and the second disease region, but the present disclosure is not limited to this. The second discriminative model and the third discriminative model may be constructed to derive the infarction region and the large vessel occlusion part without using the information of the regions symmetrical with respect to the midline of the brain in the CT image G0, the first disease region, and the second disease region.

Moreover, in each of the embodiments described above, the second discriminative model and the third discriminative model are constructed by using the U-Net, but the present disclosure is not limited to this. The second discriminative model may be constructed by using a convolutional neural network other than the U-Net.

Moreover, in each of the embodiments described above, in the first discriminative models 22A, 82A, and 83A of the information derivation units 22, 82, and 83, the first disease region (that is, the infarction region or the large vessel occlusion part) is derived from the CT image G0 by using the CNN, but the present disclosure is not limited to this. In the information derivation unit, the second disease region may be derived by acquiring, as the first disease region, a mask image generated by the doctor interpreting the CT image G0 and specifying the infarction region or the large vessel occlusion part, without using the first discriminative model.

Moreover, in each of the embodiments described above, the infarction region and the large vessel occlusion part in the brain are derived by using the non-contrast CT image of the brain as the processing target, but the present disclosure is not limited to this. For example, a discriminative model may be constructed such that a CT image of the heart is used as the processing target and an infarction region in the heart and an occlusion part of the coronary artery are derived.

Moreover, in each of the embodiments described above, the non-contrast CT image is the processing target, but the present disclosure is not limited to this. Any medical image, such as a radiation image, an MRI image, a contrast CT image, and a PET image, can be the processing target.

Moreover, in each of the embodiments described above, the information derivation units 22, 82, and 83 derive the infarction region and the large vessel occlusion part, but the present disclosure is not limited to this. A bounding box that surrounds the infarction region and the large vessel occlusion part may be derived.

Moreover, in the embodiments described above, for example, various processors shown below can be used as the hardware structures of processing units that execute various processing, such as the information acquisition unit 21, the information derivation unit 22, the learning unit 23, the quantitative value derivation unit 24, and the display controller 25 in the information processing apparatus 1. As described above, in addition to the CPU which is a generalpurpose processor that executes the software (program) to function as the various processing units described above, the various processors include a programmable logic device (PLD), which is a processor of which a circuit configuration can be changed after manufacturing, such as a field programmable gate array (FPGA), a dedicated electric circuit, which is a processor having a circuit configuration exclusively designed to execute specific processing, such as an application specific integrated circuit (ASIC), and the like.

One processing unit may be configured by one of these various processors, or may be configured by a combination of two or more processors of the same type or different types (for example, a combination of a plurality of FPGAs or a combination of the CPU and the FPGA). Moreover, a plurality of processing units may be configured by one processor. A first example of the configuration in which the plurality of processing units are configured by one processor is a form in which one processor is configured by a combination of one or more CPUs and software and the processor functions as the plurality of processing units as represented by the computer, such as a client and a server. A second example thereof is a form in which a processor that realizes the function of the entire system including the plurality of processing units by one integrated circuit (IC) chip is used, as represented by a system on chip (SoC) or the like. As described above, as the hardware structures, the various processing units are configured by using one or more of the various processors described above.

Further, as the hardware structures of these various processors, more specifically, it is possible to use an electric circuit (circuitry) in which circuit elements, such as semiconductor

What is claimed is:

1. An information processing apparatus comprising:

at least one processor, wherein the processor acquires a medical image and a first disease region in the medical image, derives a second disease region related to the first disease region in the medical image based on the medical image and the first disease region, updates the first disease region based on the medical image and the second disease region, updates the second disease region based on the medical image and the updated first disease region, repeats update of the first disease region and update of the second disease region until a predetermined end condition is satisfied, and derives the updated first disease region and the updated second disease region, respectively as a final first disease region and a final second disease region, from the medical image in a case in which the predetermined end condition is satisfied, wherein the processor performs update of the first disease region and derivation and update of the second disease region by using a first discriminative model that has been trained to output the second disease region in a case in which the medical image and the first disease region are input, and a second discriminative model that has been trained to output the first disease region in a case in which the medical image and the second disease region are input.

2. The information processing apparatus according to claim 1, wherein the processor performs update of the first disease region and derivation and update of the second disease region further based on at least one of information representing an anatomical region of an organ including the first and second disease regions or clinical information.

3. The information processing apparatus according to claim 1, wherein the processor acquires the first disease region by extracting the first disease region from the medical image.

4. The information processing apparatus according to claim 1, wherein the processor derives quantitative information for at least one of the first disease region or the second disease region, and displays the quantitative information.

5. The information processing apparatus according to claim 1, wherein the medical image is a non-contrast CT image of a brain of a patient, the first disease region is any one of an infarction region or a large vessel occlusion part in the non-contrast CT image, and the second disease region is the other of the infarction region or the large vessel occlusion part in the non-contrast CT image.

6. The information processing apparatus according to claim 5, wherein the processor performs derivation and update of the second disease region by further using first information of regions symmetrical with respect to a midline of the brain in at least the non-contrast CT image out of the non-contrast CT image and the first disease region, and performs update of the first disease region by further using second information of regions symmetrical with respect to the midline of the brain in at least the non-contrast CT image out of the non-contrast CT image and the second disease region.

7. The information processing apparatus according to claim 6, wherein the first information is first reversal information obtained by reversing at least the non-contrast CT image out of the non-contrast CT image and the first disease region with respect to the midline of the brain, and the second information is second reversal information obtained by reversing at least the non-contrast CT image out of the non-contrast CT image and the second disease region with respect to the midline of the brain.

8. An information processing method comprising:

acquiring a medical image and a first disease region in the medical image;

deriving a second disease region related to the first disease region in the medical image based on the medical image and the first disease region;

updating the first disease region based on the medical image and the second disease region;

updating the second disease region based on the medical image and the updated first disease region; repeating update of the first disease region and update of the second disease region until a predetermined end condition is satisfied; and deriving the updated first disease region and the updated second disease region, respectively as a final first disease region and a final second disease region, from the medical image in a case in which the predetermined end condition is satisfied, wherein update of the first disease region and derivation and update of the second disease region are performed by using a first discriminative model that has been trained to output the second disease region in a case in which the medical image and the first disease region are input, and a second discriminative model that has been trained to output the first disease region in a case in which the medical image and the second disease region are input.

9. A non-transitory computer-readable storage medium that stores an information processing program causing a computer to execute:

a procedure of acquiring a medical image and a first disease region in the medical image;

a procedure of deriving a second disease region related to the first disease region in the medical image based on the medical image and the first disease region;

a procedure of updating the first disease region based on the medical image and the second disease region;

a procedure of updating the second disease region based on the medical image and the updated first disease region;

a procedure of repeating update of the first disease region and update of the second disease region until a predetermined end condition is satisfied; and a procedure of deriving the updated first disease region and the updated second disease region, respectively as a final first disease region and a final second disease region, from the medical image in a case in which the predetermined end condition is satisfied, wherein update of the first disease region and derivation and update of the second disease region are performed by using a first discriminative model that has been trained to output the second disease region in a case in which the medical image and the first disease region are input, and a second discriminative model that has been trained to output the first disease region in a case in which the medical image and the second disease region are input.

10. An information processing apparatus comprising:

at least one processor, wherein the processor acquires a medical image, inputs the medical image into a first discriminative model and derive a first mask image representing a first disease region in the medical image outputted from the first discriminative model, inputs the medical image and the first mask image into a second discriminative model to derive a second mask image representing a second disease region outputted from the second discriminative model, wherein the second disease region is related to the first disease region in the medical image, inputs the medical image and the second mask image into a third discriminative model to derive an updated first mask image representing an updated first disease region in the medical image outputted by the third discriminative model, inputs the medical image and the updated first mask image to the second discriminative model to derive an updated second mask image representing an updated second disease region representing an updated second disease region in the medical image outputted by the second discriminative model, repeats update of the first disease region and update of the second disease region until a predetermined end condition is satisfied, and derives the updated first mask image and the updated second mask image, respectively as a final first disease region and a final second disease region, after the predetermined end condition is satisfied.

* * * * *